US006897177B2

(12) United States Patent
Van Berge et al.

(10) Patent No.: US 6,897,177 B2
(45) Date of Patent: May 24, 2005

(54) COBALT CATALYSTS

(75) Inventors: Peter Jacobus Van Berge, Sasolburg (ZA); Jan Van De Loosdrecht, Sasolburg (ZA); Jacobus Lucas Visagie, Sasolburg (ZA)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 1 day.

(21) Appl. No.: 10/304,465

(22) Filed: Nov. 26, 2002

(65) Prior Publication Data

US 2003/0139286 A1 Jul. 24, 2003

Related U.S. Application Data

(63) Continuation of application No. PCT/IB01/01013, filed on Jun. 11, 2001.
(60) Provisional application No. 60/210,986, filed on Jun. 12, 2000, and provisional application No. 60/215,489, filed on Jun. 30, 2000.

(51) Int. Cl.[7] .......................... B01J 21/18; B01J 21/08; B01J 23/40; B01J 23/56
(52) U.S. Cl. .................. 502/185; 502/260; 502/261; 502/262; 502/327; 502/328; 502/332; 502/333; 502/334; 502/339; 502/340; 502/341; 502/350; 502/351; 502/355; 502/415; 502/439
(58) Field of Search .................. 502/185, 260–262, 502/327, 328, 332–334, 339–341, 350, 351, 355, 415, 439

(56) References Cited

U.S. PATENT DOCUMENTS

| 5,053,574 | A | 10/1991 | Tsutsui et al. | 585/488 |
|---|---|---|---|---|
| 5,733,839 | A | 3/1998 | Espinoza et al. | 502/336 |
| 5,998,328 | A | * 12/1999 | Dawes et al. | 502/182 |
| 6,455,462 | B2 | * 9/2002 | van Berge et al. | 502/235 |
| 2001/0038814 | A1 | * 11/2001 | Fischer et al. | 423/240 S |

FOREIGN PATENT DOCUMENTS

| EP | 0069514 | 12/1983 | |
| EP | 0681868 | 11/1995 | |
| GB | 1528209 | * 11/1978 | ............ B01J/23/40 |
| WO | 9942214 | 8/1999 | |
| WO | WO 99/42214 | * 8/1999 | ............ B01J/33/00 |
| WO | 00/20116 | 4/2000 | |
| WO | 01/39882 | 6/2001 | |

OTHER PUBLICATIONS

Knözinger, H. and P. Ratnasamy, "Catalytic Aluminas: Surface Models and Characterization of Surfac Sites", *Catal. Rev. –Sci. Eng.*, (1978), 17(1): 31–70, Presented at the Fifth North American Meeting of the Catalysis Society, Pittsburgh, 1977, (no month avail.).

* cited by examiner

*Primary Examiner*—Mark L. Bell
*Assistant Examiner*—Patricia L. Hailey
(74) *Attorney, Agent, or Firm*—Ladas & Parry

(57) ABSTRACT

A process for preparing a cobalt based catalyst precursor includes, in a support impregnation stage, impregnating a coated catalyst support comprising porous catalyst support particles coated with carbon, with a cobalt salt, and partially drying the impregnated support. Thereafter, in a calcination stage, the partially dried impregnated support is calcined, to obtain the cobalt based catalyst precursor. The cobalt based catalyst precursor can then, in a reduction stage, be reduced to obtain a cobalt based Fischer-Tropsch catalyst.

12 Claims, 1 Drawing Sheet

COBALT CATALYSTS

Figure 1:
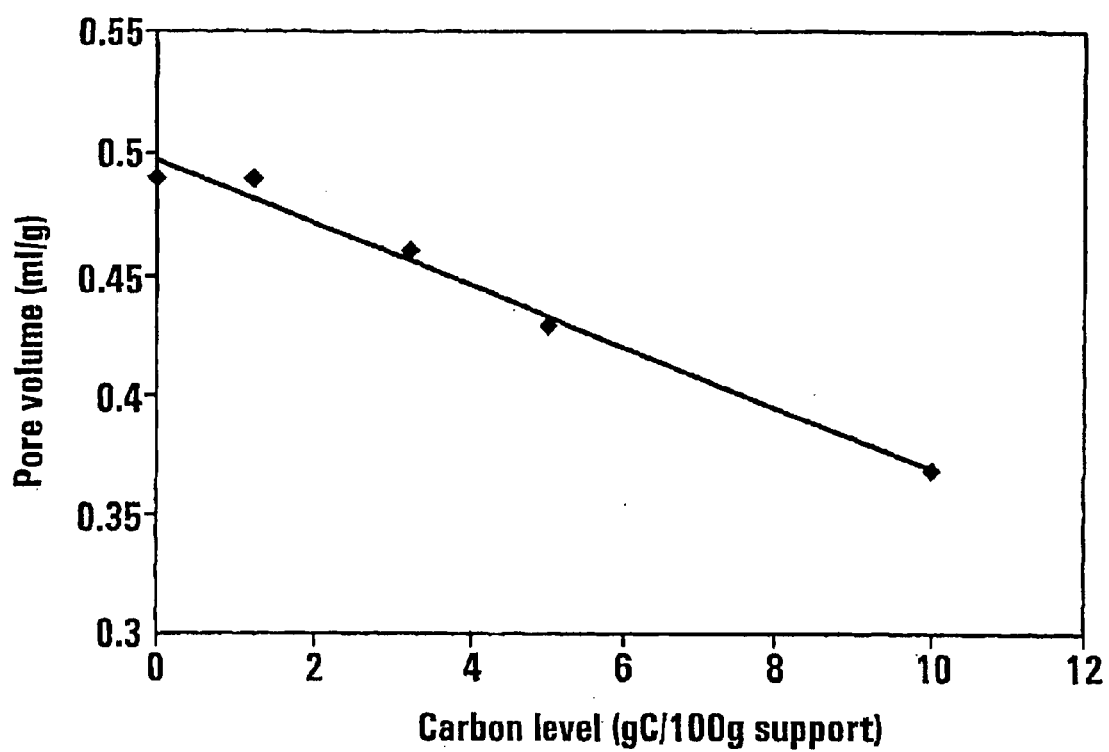

This application is a continuation of PCT/IB01/01013 filed on Jun. 11, 2001, which claims benefit of No. 60/210,986 Jun. 12, 2000 and claims benefit of No. 60/215,489 Jun. 30, 2000.

THIS INVENTION relates to cobalt catalysts. In particular, the invention relates to a process for preparing a precursor of a cobalt based Fischer-Tropsch catalyst, to a process for preparing such a cobalt catalyst, and to a process for producing hydrocarbons using such a cobalt catalyst.

The Applicant is aware of known processes for preparing cobalt based catalyst precursors and which involve slurry phase impregnation of a catalyst support with a cobalt salt, drying of the impregnated catalyst support, and calcination of the dried impregnated catalyst support, to achieve a desired cobalt loading of the support. The resultant precursors are then activated by reduction thereof, to obtain cobalt based Fischer-Tropsch catalysts. These catalysts can display good intrinsic activities when used for Fischer-Tropsch synthesis; however, catalysts having enhanced or superior intrinsic activities cannot readily be obtained using the known processes. It is thus an object of the present invention to provide a cobalt based Fischer-Tropsch catalyst having enhanced initial and/or stabilized intrinsic Fischer-Tropsch synthesis activity, as well as a process for preparing such a catalyst.

According to a first aspect of the invention, there is provided a process for preparing a cobalt based catalyst precursor, which process includes in a support impregnation stage, impregnating a coated catalyst support comprising porous catalyst support particles coated with carbon, with a cobalt salt, and partially drying the impregnated support; and in a calcination stage, calcining the partially dried impregnated support, to obtain the cobalt based catalyst precursor.

The resultant cobalt based catalyst precursor will, in practice, be reduced to obtain a cobalt based Fischer-Tropsch catalyst. It was surprisingly found that this catalyst has enhanced or superior initial as well as stabilized intrinsic Fischer-Tropsch synthesis activity.

Thus, according to a second aspect of the invention, there is provided a process for preparing a cobalt based Fischer-Tropsch-catalyst, which process includes in a support impregnation stage, impregnating a coated catalyst support comprising porous catalyst support particles coated with carbon, with a cobalt salt, and partially drying the impregnated support;

in a calcination stage, calcining the partially dried impregnated support, to obtain a cobalt based catalyst precursor; and in a reduction stage, reducing the cobalt based catalyst precursor to obtain the cobalt based Fischer-Tropsch catalyst.

If a higher cobalt loading is required, then a second, or even a third, impregnation, drying and calcination step may thereafter be carried out after the first impregnation, drying and calcination step hereinbefore described.

In this specification, unless explicitly otherwise stated, where reference is made to catalyst mass, the mass given pertains to the calcined catalyst mass, ie the catalyst mass before any reduction of the catalyst is effective.

The cobalt salt may, in particular, be cobalt nitrate, $Co(NO_3)_2 \cdot 6H_2O$.

The carbon coated catalyst support may be any commercially available porous oxidic catalyst support, such as alumina ($Al_2O_3$), silica ($SiO_2$), a silica alumina ($SiO_2 \cdot Al_2O_3$), titania ($TiO_2$) and magnesia (MgO), coated with carbon.

The support may be a protected modified catalyst support, containing, for example, silicon as a modifying component, as described in WO 99/42214 and which is hence incorporated herein by reference.

The processes according to the first and second aspects may, if necessary, include preparing the carbon coated catalyst support, ie they may include modifying the porous catalyst support particles by coating them with carbon.

In principle, the coating of the catalyst support particles can then be effected by any suitable method. For example, the carbon coated catalyst support may be prepared by coating pre-shaped spherical porous catalyst support particles with a uniform carbon based layer in accordance with the method as described in EP 0681868, which is hence incorporated herein by reference.

It is to be appreciated that the maximum amount of carbon that can be used as an effective coating is determined by the influence of the carbon coating on the pore volume of the original catalyst support, as the pore volume of the catalyst support determines how much cobalt can be impregnated into the catalyst support. This is particularly important when catalysts with a relatively high cobalt loading are required. Similarly, the minimum amount of carbon that can be used as an effective coating is determined by the minimum level of carbon that still provides the required positive effect on the stabilized intrinsic Fischer-Tropsch synthesis performance of the resultant cobalt catalyst. Thus, the maximum level of carbon may be 40 g C/100 g support, preferably 20 g C/100 g support, and more preferably 10 g C/100 g support, while the minimum level of carbon may be 0.1 g C/100 g support, preferably 0.5 g C/100 g support, and more preferably 1.2 g C/100 g support.

The support impregnation with the cobalt salt may, in principle, be effected by any known impregnation method, eg incipient wetness impregnation, or slurry phase impregnation. Similarly, the calcination may be performed in any known calcination unit, eg fluidized bed, fixed bed, furnace, rotary kiln, and/or torbed calciner, preferably at temperatures between 150° C. and 300° C. In particular, the calcination may be in accordance with that described in PCT/IB00/01745, and which is thus incorporated herein by reference. The calcination may thus involve fluidized bed calcination as described in PCT/IB00/01745.

The cobalt catalyst precursor may be obtained by a 2-step slurry phase impregnation, drying and calcination process. The 2-step process may include, in a first step, impregnating the carbon coated catalyst support with the cobalt salt, partially drying the impregnated support, and calcining the partially dried support, to obtain a calcined material, and thereafter, in a second step, impregnating the calcined material with the cobalt salt, partially drying the impregnated material, and calcining the partially dried material, to obtain the catalyst precursor.

The support impregnation with the cobalt salt, the drying and the calcination may, in particular, be in accordance with the process described in our copending WO 00/20116, which is thus incorporated herein by reference.

The support impregnation and drying may typically be effected in a conical vacuum drier with a rotating screw or in a tumbling vacuum drier.

The catalyst precursor may contain between 5 g Co/100 g support and 70 g Co/100 g support, preferably between 20 g Co/100 g support and 50 g Co/100 g support.

During either or both of the slurry phase impregnation steps, a water soluble precursor salt of palladium (Pd) or platinum (Pt) or a mixture of such salts may be added, as a dopant capable of enhancing the reducibility of the cobalt. Preferably, the dopant is added in a mass proportion of the palladium metal, the platinum metal or the mixture of palladium and platinum metals to the cobalt metal of between 0.01:100 to 0.3:100.

The invention extends also to a cobalt catalyst, when produced by the process of the second aspect of the invention, and to a cobalt catalyst precursor, when produced by the process of the first aspect of the invention.

According to a third aspect of the invention, there is provided a process for producing hydrocarbons, which includes contacting synthesis gas comprising hydrogen ($H_2$) and carbon monoxide (CO) at an elevated temperature between 180° C. and 250° C. and an elevated pressure between 1 and 40 bar with a cobalt catalyst according to the invention, in a slurry phase Fischer-Tropsch reaction of the hydrogen with the carbon monoxide, to obtain hydrocarbons.

The invention extends also to hydrocarbons when produced by the process as hereinbefore described.

The invention will now be described in more detail with reference to the following non-limiting examples and with reference to the accompanying drawing.

In the drawing,

FIG. 1 shows the influence of carbon levels on the pore volume of the carbon-coated catalyst support.

EXAMPLE 1

Catalyst B (30 g Co/100 g $Al_2O_3$) (Not in Accordance with the Invention)

Preparation

A Pt promoted catalyst was prepared on SASOL Germany GmbH's trademark product: Puralox SCCa 5/150, as a selected pre-shaped $Al_2O_3$ support, in accordance with the method of aqueous slurry phase impregnation and vacuum drying, followed by direct fluidized bed calcination, in accordance with Catalyst Example 1 of WO 00/20116, or one of Catalysts D, E, G or H of PCT/IB00/01745.

In preparation for laboratory scale slurry phase continuous stirred tank reactor ('CSTR') Fischer-Tropsch synthesis runs, this calcined material was reduced and wax coated in accordance with the following procedure:

27.5 g of the catalyst was reduced at 1 bar pure $H_2$ (space velocity≧200 ml$_n$ $H_2$/g catalyst/h) whilst the temperature was increased from 25° C. to 380° C.–425° C. at a rate of 1° C./min whereafter the temperature was kept constant at this temperature of 380° C.–425° C. for 16 hours.

The reduced catalyst was allowed to cool down to room temperature at which stage the hydrogen was replaced by argon, and the catalyst unloaded in molten Fischer-Tropsch wax under the protection of an argon blanket. This wax coated catalyst was then transferred to the slurry reactor.

CSTR Fischer-Tropsch Synthesis Run

An extended slurry phase CSTR Fischer-Tropsch synthesis run (number 106F) was performed on catalyst B. This run lasted about ('ca') 90 days, during which the following synthesis conditions were maintained:

| Reactor temperature | 220.5° C. |
|---|---|
| Reactor pressure | 20.3 bar |
| Catalyst inventory | 20.8 g |
| ($H_2$ + CO) space velocity | 2169 ml$_n$/(g catalyst.h) |
| APG space velocity | 2452 ml$_n$/(g catalyst.h), | where 'APG' is an acronym for Arge Pure Gas, ie the commercial synthesis gas produced at Schumann-Sasol (Pty) Limited in Sasolburg, South Africa, according to the method of coal gasification, followed by Rectisol (trademark) purification.

| Feed gas composition: | |
|---|---|
| $H_2$ | 49.1 vol % |
| CO | 25.9 vol % |
| $CH_4$ | 9.3 vol % |
| $CO_2$ | 0.5 vol % |
| Ar | 15.2 vol % |

The observed synthesis performance data of this run (i.e. 106F) is presented in Table 1.

Relative (Fischer-Tropsch) Intrinsic Activity Factor ('R.I.A.F.') is defined as follows:

Consider an arbitrary slurry phase cobalt Fischer-Tropsch catalyst, displaying the following observed synthesis performance in a CSTR:

$T_{FT}$=Z moles CO converted to Fischer-Tropsch products per gram catalyst per second, observed at T=y Kelvin, at the following set of reactor partial pressures:

$P_{H2}$=ν bar $P_{CO}$=τ bar then the definition of R.I.A.F. is as follows:

$$R.I.A.F=[Z(1+1.82\tau)^2]/[49480.9e^{(-11113.4/y)}\nu\tau]$$

Initial intrinsic Fischer-Tropsch activity ($a_i$) of a slurry phase cobalt based catalyst is defined as follows:

$a_i$=the R.I.A.F. after 15 hours on stream (ie $t_i$=time initial) of continuous exposure to the following set of gradientless slurry phase synthesis conditions:

220° C., 20 bar, %($H_2$+CO) conversion in excess of 50%, obtained with a feed gas of composition: ca 50 vol % $H_2$ and ca 25 vol % CO, the balance consisting of Ar, $N_2$, $CH_4$ and/or $CO_2$.

Catalyst C (C239) (40 g Co/100 g $Al_2O_3$) (Not in Accordance with the Invention)

Preparation

Catalyst C was prepared in a similar manner as catalyst B. The only difference was that catalyst C was prepared by three consecutive impregnation/drying/calcination steps and catalyst B by two steps. This was done to increase the cobalt loading from 30 to 40 g/100 g $Al_2O_3$.

Catalyst C was also tested for Fischer-Tropsch synthesis (run 293F) performance and the results are presented in Table 1.

TABLE 1

| | Catalyst | |
|---|---|---|
| | C | B |
| Catalyst characteristics: | | |
| Composition | 40 gCo/0.100 gPt/ 100 gAl$_2$O$_3$ | 30 gCo/0.075 gPt/ 100 gAl$_2$O$_3$ |
| Synthesis performance data: | | |
| Run analysis number | 293F | 106F |
| Time on stream (hours) | 15 | 15.5 |
| % (H$_2$ + CO) conversion | 65 | 73 |
| Reactor partial pressures: | | |
| H$_2$ (bar) | 5.3 | 3.7 |
| CO (bar) | 2.8 | 2.4 |
| H$_2$O (bar) | 4.7 | 5.0 |
| CO$_2$ (bar) | 0.4 | 0.3 |
| Initial Relative Intrinsic (Fischer-Tropsch) Activity Factor (i.e.: a$_i$ = R.I.A.F. at t$_i$) | 3.5 | 2.7 |

EXAMPLE 2

Examples of Al$_2$O$_3$ Supported Cobalt Slurry Phase Catalyst Samples in Accordance with the Invention (Catalysts E, K, L) that Displayed Enhanced Initial Intrinsic Fischer-Tropsch Activities Catalyst E (40 g Co/0.100 g Pt/100 g Al$_2$O$_3$)
Preparation SASOL Germany GmbH's trademark product: Puralox SCCa 5/150 (ie a pre-shaped spherical porous Al$_2$O$_3$ catalyst support material), was coated with a uniform carbon based layer at KataLeuna GmbH Catalysts (Am Haupttor; D-06236 Leuna; Germany) in accordance with a method as described in EP 0681868, incorporated herein by reference. The result of this exercise was a 12.4 g C/100 g Al$_2$O$_3$ modified support.

A 40 g Co/0.100 g Pt/100 g Al$_2$O$_3$ slurry phase Fisher-Tropsch catalyst was prepared on this modified 12.4 g C/100 g Al$_2$O$_3$ pre-shaped support material in accordance with the method of aqueous slurry phase impregnation and vacuum drying, followed by direct fluidized bed calcination disclosed in U.S. Pat. No. 5,733,839, WO 99/42214 and WO 00/20116, incorporated herein by reference. In particular, catalyst E was prepared as follows:

34.1 g Co(NO$_3$)$_2$.6H$_2$O was dissolved in 40 ml distilled water and 0.0185 g (NH$_3$)$_4$Pt(NO$_3$)$_2$ was dissolved in 10 ml distilled water. These two solutions were mixed together in a 500 ml round ball flask in a rotavapor at 60° C. and atmospheric pressure, and 50 g of the 12.4 g C/100 g Al$_2$O$_3$ modified support was added. Aqueous slurry phase impregnation and vacuum drying was effected via the following procedure:

| Temperature of oil bath (° C.) | Rotavapor pressure (mbar) | Time (minutes) |
|---|---|---|
| 60 | Atmospheric | 10 |
| 60 | 240 | 30 |
| 70 | 240 | 90 |
| 85 | 240 | 60 |
| 85 | 50 | 240 |

This vacuum dried intermediate product was directly subjected to a fluidized bed calcination step, having followed the following procedure:

Continuous air flow of 1.7 dm$^3_n$/min
Temperature program:

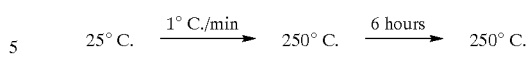

50 g of this intermediate calcined material was subjected to the following 2$^{nd}$ cobalt/platinum impregnation and calcination step:

34.1 g Co(NO$_3$)$_2$.6H$_2$O was dissolved in 40 ml distilled water and 0.0189 g (NH$_3$)$_4$Pt(NO$_3$)$_2$ was dissolved in 10 ml distilled water. These two solutions were mixed together in a 500 ml round ball flask in a rotavapor at 60° C. and atmospheric pressure, and 50 g of the ex 1$^{st}$ impregnated and calcined intermediate was added Aqueous slurry phase impregnation and vacuum drying was effected in the same manner as during the 1$^{st}$ cobalt/platinum impregnation step. This vacuum dried intermediate product was directly subjected to a fluidized bed calcination step, having followed the following procedure:

Continuous air flow of 1.7 dm$^3_n$/min
Temperature program:

50 g of this intermediate calcined material was subjected to the following 3$^{rd}$ cobalt/platinum impregnation and calcination step:

25.4 g Co(NO$_3$)$_2$.6H$_2$O was dissolved in 40 ml distilled water and 0.0446 g (NH$_3$)$_4$Pt(NO$_3$)$_2$ was dissolved in 10 ml distilled water. These two solutions were mixed together in a 500 ml round ball flask in a rotavapor at 60° C. and atmospheric pressure, and 50 g of the ex 2$^{nd}$ impregnated and calcined intermediate was added. Aqueous slurry phase impregnation and vacuum drying was effected in the same manner as during the 1$^{st}$ cobalt/platinum impregnation step. This vacuum dried intermediate product was directly subjected to a fluidized bed calcination step, having followed the following procedure:

Continuous air flow of 1.7 dm$^3_n$/min
Temperature program:

A total of three consecutive impregnation steps were thus performed as dictated by the restrictions imposed by the pore volume of the solid materials.

In preparation for laboratory scale slurry phase CSTR Fischer-Tropsch synthesis runs, this calcined catalyst precursor was reduced externally at 350° C. For this purpose 22.8 g of the catalyst was reduced at 1 bar pure H$_2$ (space velocity of 2000 ml$_n$/g catalyst.h), whilst the temperature was increased from 25° C. to 350° C. at a rate of 1° C./min, where-after the temperature was kept constant at 350° C. for 16 hours.

The reduced catalyst was allowed to cool down to room temperature where the hydrogen was replaced by argon and the catalyst was unloaded in molten wax under the protection of an argon blanket. This wax coated catalyst was then transferred to the slurry synthesis reactor.

Catalyst K (C258) (30 g Co/0.075 g Pt/1.5 g Si/100 g Al$_2$O$_3$)
Preparation

SASOL Germany GmbH's trademark product: Siralox 1.5 (i.e. a pre-shaped spherical porous Al$_2$O$_3$ catalyst support material, containing 1.5 m % SiO$_2$), was coated with a uniform carbon based layer at KataLeuna GmbH Catalysts (Am Haupttor; D-06236 Leuna; Germany) in accordance with the method as described in EP 0681868, which is incorporated herein by reference. The result of this exercise was a 12.4 g C/100 g Al$_2$O$_3$ modified support.

A 30 g Co/0.075 g Pt/1.5 g Si/100 g Al$_2$O$_3$ slurry phase Fischer-Tropsch catalyst was prepared on this modified 12.4 g C/1.5 g Si/100 g Al$_2$O$_3$ pre-shaped support material in accordance with the method of aqueous slurry phase impregnation and vacuum drying, followed by direct fluidized bed calcination disclosed in U.S. Pat. No. 5,733,839, WO 99/42214 and WO 00/20116, incorporated herein by reference.

Catalyst K was thus prepared in a similar manner to Catalyst E, the only difference being the lower cobalt loading of catalyst K, i.e. 30 versus 40 g Co/100 g Al$_2$O$_3$, which was achieved in two impregnation/drying/calcination steps.

Catalyst L (C339) (30 g Co/0.075 g Pt/1.5 g Si/100 g Al$_2$O$_3$) Preparation

SASOL Germany GmbH's trademark product: Siralox 1.5 (i.e. a pre-shaped spherical porous Al$_2$O$_3$ catalyst support material, containing 1.5 m % SiO$_2$), was coated with a uniform carbon based layer at KataLeuna GmbH Catalysts (Am Haupttor; D-06236 Leuna; Germany) in accordance with a method as described in EP 0681868, incorporated herein by reference. The result of this exercise was a 1.2 g C/100 g Al$_2$O$_3$ modified support.

A 30 g Co/0.075 g Pt/1.5 g Si/100 g Al$_2$O$_3$ slurry phase Fischer-Tropsch catalyst was prepared on this modified 1.2 g C/1.5 g Si/100 g Al$_2$O$_3$ pre-shaped support material in accordance with the method of aqueous slurry phase impregnation and vacuum drying, followed by direct fluidized bed calcination disclosed in U.S. Pat. No. 5,733,839, WO 99/42214 and WO 00/20116, incorporated herein by reference.

Catalyst L was thus prepared in a similar manner to Catalyst K, the only difference being the lower carbon loading of the support used for catalyst L, i.e. 1.2 g C versus 12.4 g C/100 g Al$_2$O$_3$.

The pore volumes of the (carbon coated) catalyst supports used to prepare catalysts B, C, E, K, and L are presented in FIG. 1 as a function of the amount of carbon on the catalyst support. It can be seen that the pore volumes of the catalyst supports decrease with increasing levels of carbon.

Catalysts E, K, and L were tested for their Fischer-Tropsch synthesis performance in a similar manner to that described in Example 1. The observed results are presented in Table 2.

TABLE 2

| | Catalyst | | |
|---|---|---|---|
| | E | K | L |
| Catalyst characteristics: | | | |
| Composition | 40 gCo/0.100 gPt/ 100 gAl$_2$O$_3$ | 30 gCo/0.075 gPt/ 1.5 gSi/ 100 gAl$_2$O$_3$ | 30 gCo/0.075 gPt/ 1.5 gSi/ 100 gAl$_2$O$_3$ |
| Synthesis performance data: | | | |
| Run analysis number | 45£ | 55£ | 97£ |
| Time on stream (hours) | 15 | 15 | 15 |
| % (H$_2$ + CO) conversion | 76 | 54 | 72 |
| Reactor partial pressures: | | | |
| H$_2$ (bar) | 4.0 | 6.5 | 4.1 |
| CO (bar) | 2.3 | 3.5 | 2.0 |
| H$_2$O (bar) | 5.9 | 3.8 | 4.5 |
| CO$_2$ (bar) | 0.5 | 0.3 | 0.4 |
| Initial Relative Intrinsic (Fischer-Tropsch) Activity Factor (ie: a$_i$ = R.I.A.F. at t$_i$) | 5.6 | 4.3 | 4.0 |

The following conclusions can be drawn from Tables 1 and 2:

Catalyst E, ie 40 g Co/0.100 g Pt/100 g Al$_2$O$_3$ prepared on an alumina support coated with carbon, displayed an initial RIAF of 5.6, which is significantly higher than the initial RIAF of 3.5 of catalyst C, i.e. 40 g Co/0.100 g Pt/100 g Al$_2$O$_3$ prepared on an alumina support without carbon coating.

Catalysts K and L, i.e. both 30 g Co/0.075 g Pt/100 g support and both prepared on an carbon coated alumina support, displayed significantly higher initial RIAF's, ie 4.3 and 4.0 respectively, than the initial RIAF of 2.7 of catalyst B, ie 30 g Co/0.075 g Pt/100 g Al$_2$O$_3$ prepared on an alumina support without carbon coating.

In this invention it was thus surprisingly found that cobalt based Fischer-Tropsch synthesis catalysts displayed an increased intrinsic catalytic performance when these catalysts were prepared on supports which were carbon coated prior to the deposition of the active cobalt phase onto and into the support during the impregnation/drying step.

What is claimed is:

1. A process for preparing a cobalt based catalyst precursor, which process includes
    in a support impregnation stage, impregnating a coated catalyst support comprising porous catalyst support particles coated with carbon, with a cobalt salt, and partially drying the impregnated support; and
    in a calcination stage, calcining the partially dried impregnated support, to obtain the cobalt based catalyst precursor.

2. A process according to claim 1, wherein the amount of carbon present on the support is from 0.1 g carbon/100 g support to 20 g carbon/100 g support.

3. A process according to claim 1, wherein the cobalt salt is cobalt nitrate, and wherein the porous catalyst support particles are alumina, silica, silica-alumina, titania or magnesia particles.

4. A process according to claim 1, wherein the support is a protected modified catalyst support containing silicon as a modifying component.

5. A process according to claim 1, wherein the cobalt catalyst precursor is obtained by a 2-step slurry phase impregnation, drying and calcination process which includes, in a first step, impregnating the carbon coated catalyst support with the cobalt salt, partially drying the impregnated support, and calcining the partially dried support, to obtain a calcined material, and thereafter, in a second step, impregnating the calcined material with the cobalt salt, partially drying the impregnated material, and calcining the partially dried material, to obtain the catalyst precursor.

6. A process according to claim 5 wherein, during either or both of the two slurry phase impregnation steps, a water soluble precursor salt of palladium or platinum or a mixture of such salts is added, as a dopant capable of enhancing the reducibility of the cobalt.

7. A process for preparing a cobalt based Fischer-Tropsch catalyst, which process includes
- in a support impregnation stage, impregnating a coated catalyst support comprising porous catalyst support particles coated with carbon, with a cobalt salt, and partially drying the impregnated support;
- in a calcination stage, calcining the partially dried impregnated support, to obtain a cobalt based catalyst precursor; and
- in a reduction stage, reducing the cobalt based catalyst precursor to obtain the cobalt based Fischer-Tropsch catalyst.

8. A process according to claim 7, wherein the amount of carbon present on the support is from 0.1 g carbon/100 g support to 20 g carbon/100 g support.

9. A process according to claim 7, wherein the cobalt salt is cobalt nitrate, and wherein the porous catalyst support particles are alumina, silica, silica-alumina, titania or magnesia particles.

10. A process according to claim 7, wherein the support is a protected modified catalyst support containing silicon as a modifying component.

11. A process according to claim 7, wherein the cobalt catalyst precursor is obtained by a 2-step slurry phase impregnation, drying and calcination process which includes, in a first step, impregnating the carbon coated catalyst support with the cobalt salt, partially drying the impregnated support, and calcining the partially dried support, to obtain a calcined material, and thereafter, in a second step, impregnating the calcined material with the cobalt salt, partially drying the impregnated material, and calcining the partially dried material, to obtain the catalyst precursor.

12. A process according to claim 11 wherein, during either or both of the two slurry phase impregnation steps, a water soluble precursor salt of palladium or platinum or a mixture of such salts is added, as a dopant capable of enhancing the reducibility of the cobalt.

* * * * *